United States Patent [19]

Grohe et al.

[11] Patent Number: 4,659,603
[45] Date of Patent: Apr. 21, 1987

[54] IMMUNOSTIMULATING AGENTS

[75] Inventors: Klaus Grohe, Odenthal; Volker Klimetzek, Velbert; Karl G. Metzger; Klaus G. Stünkel, both of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 735,494

[22] Filed: May 17, 1985

[30] Foreign Application Priority Data

May 30, 1984 [DE] Fed. Rep. of Germany ....... 3420116

[51] Int. Cl.$^4$ .................... A61K 39/00; A61K 31/495
[52] U.S. Cl. ........................................ 424/88; 424/89; 424/90; 424/91; 424/92; 514/254; 514/885
[58] Field of Search .................................. 424/88-92; 514/254, 885

[56] References Cited

U.S. PATENT DOCUMENTS 4,556,658 12/1985 Grohe et al. ...................... 514/236
4,588,726 5/1986 Petersen et al. .................... 514/254

FOREIGN PATENT DOCUMENTS 0059698 9/1982 European Pat. Off. .
2806879 8/1979 Fed. Rep. of Germany .
2342067 2/1977 France .

OTHER PUBLICATIONS

Forsgren et al., "Quinalones Affect Thymidine Incorporation into the DNA . . . Lymphocytes", *Antimicrob. Agents Chemother.*, 29(3) (1986), pp. 506-508.
Gollapudi et al., "Effect of Ciprofloxacin on Mitogen-Stimulated Lymphocyte Production", *Antimicrob. Agents Chemother.*, 29(2) (1986), pp. 337-338.
Duncker et al., "Effect of Ciprofloxacin . . . on Phagocytic Human Neutrophilic Granulocytes . . .", *Antimikrob. Antineoplast. Chemother.*, 3(5), pp. 633-635, 1984.
Duncker et al., "Influence of Various Antimicrobial Agents on . . . Granulocytes", *Chemotherapy* (Basel) (1986), 32(1), pp. 18-24.

*Primary Examiner*—John Kight, III
*Assistant Examiner*—Garnette D. Draper
*Attorney, Agent, or Firm*—Sprung Horn Kramer & Woods

[57] ABSTRACT

1-Cyclopropylquinolone-3-carboxylic acids of the formula

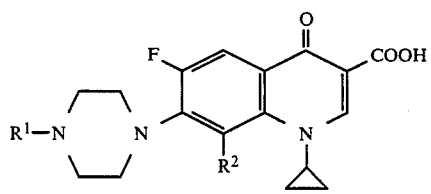

in which
  $R^1$ is hydrogen, methyl, ethyl or $\beta$-hydroxyethyl, and
  $R^2$ is hydrogen, chlorine or fluorine
or salts thereof stimulate the immune system, especially in conjunction with an antigen.

8 Claims, No Drawings

IMMUNOSTIMULATING AGENTS

The present invention relates to immunostimulating agents which contain known 1-cyclopropylquinolone-3-carboxylic acids of the general formula I

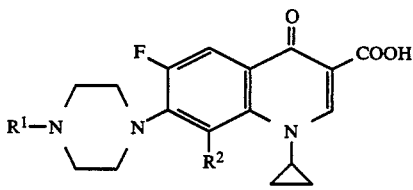

in which
R[1] represents hydrogen, methyl, ethyl or β-hydroxyethyl, and
R[2] represents hydrogen, chlorine or fluorine, and/or their physiologically tolerated acid addition salts and alkali metal salts.

It has already been disclosed that certain 1-cyclopropylquinolone-3-carboxylic acids have good antibacterial effects (DE-OS [German Published Specification] No. 3,142,854).

It has now been found that the known 1-cyclopropylquinolone-3-carboxylic acids of the general formula I and their physiologically tolerated acid addition salts and alkali metal salts have immunostimulating effects. Surprisingly, in addition to the very good antibacterial effects, they have the abovementioned immunostimulating effects to a greater extent than do known immunostimulating substances. Thus, the agents according to the invention represent an enrichment of pharmacy.

The active compounds of the general formula I, according to the invention, are known (DE-OS [German Published Specification] No. 3,142,854, DE-OS [German Published Specification] No. 3,033,157) and DE-OS (German Published Specification No. 33 18 145).

The following may be particularly mentioned as active compounds:
1-cyclopropyl-6-fluoro-1,4-dihydro-4-oxo-7-(1-piperazinyl)-3-quinolinecarboxylic acid (ciprofloxacin);
1-cyclopropyl-6-fluoro-1,4-dihydro-4-oxo-7-(4-ethyl-1-piperazinyl)-3-quinolinecarboxylic acid;
1-cyclopropyl-6,8-difluoro-1,4-dihydro-4-oxo-7-(1-piperazinyl)-4-quinolinecarboxylic acid;
1-cyclopropyl-6,8-difluoro-1,4-dihydro-4-oxo-7-(4-methyl-1-piperazinyl)-3-quinolinecarboxylic acid.

The following groups of patients, for example, can be treated successfully with the agents according to the invention:

Patients who suffer from immune deficiencies related to infection or age, induced by tumors or caused by cytostatic agents.

In addition, postoperative and post-traumatic deficiencies of the immunological defences occur. The treatment of patients with acquired immune deficiencies of this type is as yet unsatisfactory.

All these patients require medications which support or normalize the body's own defences.

The present invention includes pharmaceutical formulations which, in addition to non-toxic, inert pharmaceutically suitable vehicles, contain one or more active compounds according to the invention or which consist of one or more active compounds according to the invention, and processes for the preparation of these formulations.

The present invention also includes pharmaceutical formulations in dosage units. This means that the formulations are in the form of individual parts, for example tablets, coated tablets, capsules, pills, suppositories and ampules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable vehicles there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical formulations.

Tablets, coated tablets, capsules, pills and granules can contain the active compound or compounds alongside the customary vehicles such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrating agents, for example agar-agar, calcium carbonate and sodium bicarbonate, (e) solution retarders, for example paraffin, and (f) absorption accelerators, for example quaternary ammonium compounds, (g) wetting agents, for example cetyl alcohol or glycerol monostearate, (h) adsorbents, for example kaolin and bentonite, and (i) lubricants, for example talc, calcium stearate and magnesium stearate and solid polyethylene glycols, or mixtures of these substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned vehicles, can also be in a microencapsulated form.

Suppositories can contain, in addition to the active compound or compounds, the customary water-soluble or water-insoluble vehicles, for example polyethylene glycols, fats, for example cacao fat, and higher esters (for example $C_{14}$-alcohol with $C_{16}$-fatty acid) or mixtures of these substances.

Ointments, pastes, creams and gels can contain the customary vehicles in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary vehicles in addition to the active compound or compounds, for example lactose, talc, silica, aluminum hydroxide, calcium silicate and polyamide powders or mixtures of these substances. Sprays can additionally contain the customary propellants, for example chlorofluorohydrocarbons.

Solutions and emulsions can contain the customary vehicles in addition to the active compound or compounds, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary vehicles in addition to the active compound or compounds, such as liquid diluents, for example water, ethyl alcohol or propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colorants, preservatives and additives which improve the odor and flavor, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the usual manner according to known methods, for example by mixing the active compound or compounds with the vehicle or vehicles.

The present invention also includes the use of the active compounds according to the invention and of pharmaceutical formulations which contain one or more active compounds according to the invention, in human and veterinary medicine for the prevention, amelioration and/or cure of the abovementioned illnesses.

The active compounds or the pharmaceutical formulations can be administered locally, orally, parenterally, intraperitoneally and/or rectally, preferably parenterally, especially intravenously.

In general it has proved advantageous, both in human medicine and in veterinary medicine, to administer the active compound or compounds in amounts of about 10 to about 300, preferably 2.5 to 25, mg/kg of body weight every 24 hours, optionally in the form of several individual administrations, in order to achieve the desired results.

However, it can be necessary to deviate from the dosages mentioned and in particular to do so as a function of the nature and body weight of the subject to be treated, the nature and severity of the illness, the nature of the formulation and of the administration of the medicament, and the time or interval over which the administration takes place. Thus it can suffice in some cases to manage with less than the abovementioned amount of active compound, while in other cases the abovementioned amount of active compound must be exceeded.

The particular required optimum dosage and the type of administration of the active compounds can easily be decided by anyone skilled in the art, on the basis of his expert knowledge.

The active compounds according to the invention have a pronounced effect increasing the defenses. They increase in an antigen-specific manner the humoral, antibody-mediated and cell-mediated defenses of the immune system.

These results were obtained using the following design of experiment:

1. Increase in the primary humoral immunity in vivo toward the soluble antigen ovalbumin using ciprofloxacin as an example.

NMRI mice were immunized subcutaneously (s.c.) with a suboptimal dose of antigen (1 µg/animal, day 0). With suboptimal antigenic stimulation, only a small number of lymphocytes of the animals are stimulated to synthesize antibodies. Additional treatment of the animals with ciproflocacin is able, on single administration of 10–80 mg/kg subcutaneously, to increase slightly, but significantly, the antibody titre in the serum of the animals (Table 1). The antibodies were determined by indirect haemagglutination on day 10. The effect of the treatment is expressed by the geometric mean of $\log_2$ titre.

The immunostimulating effect of ciprofloxacin is dependent on the antigen, in contrast to other, for example, bacterial immunostimulants, such as LPS from Gram-negative bacteria, that is to say the substance induces synthesis of antibodies only in conjunction with an antigenic stimulus (ovalbumin in this case).

2. Increase in the non-specific, mitogen-induced stimulation of mouse spleen lymphocytes (MSL).

Balb/c mice were pretreated for 7 days with various s.c. doses of ciprofloxacin. SL of animals pretreated in this manner were stimulated on the 8th day ex vivo with the T-cell mitogens ConA (5 µg/ml) and PHA (10 µg/ml). After 48 hours, the cultures were labelled with $^3$H-thymidine for a further 16 hours, and were harvested. The incorporation of the radioactive thymidine in the newly synthesized DNA is taken as a measure of the lymphocyte proliferation which has occurred. The results show a marked increase in proliferation within the dose range 1–80 mg/kg (Table 2).

TABLE 1

Effect of ciprofloxacin on the synthesis of antibodies against the soluble antigen ovalbumin

| Active compound | Dose (mg/kg) | | | | | |
|---|---|---|---|---|---|---|
| | 0 | 1 | 5 | 10 | 20 | 80 |
| | Haemagglutination titre $\log_2$ | | | | | |
| Ciprofloxacin | 4.6 | 4.8 | 4.8 | 5.4[1] | 5.4[1] | 5.4[1] |

[1] Statistically significant $p < 0.05$

TABLE 2

Non-specific mitogen stimulation of mouse spleen lymphocytes in mice pretreated with ciprofloxacin

| Dose (mg/kg) | Experiment 1 | | | Experiment 2 | | |
|---|---|---|---|---|---|---|
| | ConA | PHA | 0 | ConA | PHA | 0 |
| | $^3$H—thymidine incorporation (CPM) | | | | | |
| 0 | 49,208 | 39,620 | 455 | 57,148 | 32,372 | 1,228 |
| 1 | 122,421 | 37,093 | 424 | 84,374 | 29,056 | 2,534 |
| 5 | 79,249 | 75,686 | 320 | 84,368 | 45,400 | 640 |
| 20 | 57,009 | 46,289 | 342 | 68,826 | 34,827 | 416 |

TABLE 2-continued

| | Non-specific mitogen stimulation of mouse spleen lymphocytes in mice pretreated with ciprofloxacin | | | | | |
|---|---|---|---|---|---|---|
| | Experiment 1 | | | Experiment 2 | | |
| Dose (mg/kg) | ConA | PHA | 0 | ConA | PHA | 0 |
| 80 | 60,963 | 42,286 | 620 | 61,780 | 22,818 | 700 |

A similar proliferation behavior was also achieved on treatment in vitro of the MSL mitogen cultures of non-pretreated mice.

3. Increase in the specific T-cell-mediated, allogeneic immune response (mixed lymphocyte culture—MLC) of MSL C 57 bl mice were pretreated for 7 days with various s.c. doses of ciprofloxacin. Spleens of animals pretreated in this manner were suspended on the 8th day after removal, and T-lymphocytes from each of these suspensions were enriched by passage through a nylon wool column (modified method of S. A. Eisen, H. J. Wedner and C. W. Parker, Immunological Communications 1, 571 [1972]).

These T-cell fractions were used as responders in the one-way MLC. The stimulator cells used were MS cells of D8A mice treated with mitomycin C. After 72 hours, $^3$H-thymidine was added to the cultures which were harvested after a further 16 hours (modified method of D. B. Amos and F. K. Bach, J. Exp. Med. 128, 623 [1968]). Measurements of the incorporation of $^3$H-thymidine in this test system again showed a significant increase in proliferation compared with the control in the dose range 1–80 mg/kg.

Treatments in vitro of cultures of this type from non-pretreated animals likewise result in an increased proliferation of T-lymphocytes in the dose range 0.01–10 μg of substance per ml.

4. Mitogenic and allogeneic T-lymphocyte activation of human blood lymphocytes (PBL).

Lymphocytes for this purpose were isolated by density gradient centrifugation from the heparinized blood of healthy donors. The cells thus obtained were cultured in parallel batches with the mitogens PHA (5 μg/ml) and ConA (5 μg/ml)±the selected substance, reacted with $^3$H-thymidine after 72 hours, and harvested after a further 16 hours. Increases in response to the mitogen were observed in the dose range 1–30 μg of substance per ml (Table 3).

Isolated, unfractionated PBL which were simultaneously activated in the one-way MCL using the substance, selected as an example, of the derivatives described above, at various doses, show, after culturing for 136 hours, increases in proliferation compared with the controls in the dose range 0.1–30 μg of substance per ml (Table 4).

In contrast to other, conventional immunostimulants, such as, for example, LPS mentioned above, these compounds have no mitogenic properties, that is to say they act only in conjunction with an additional induced stimulus.

TABLE 3

| | Effect of ciprofloxacin on the non-specific, mitogenic activation of human blood lymphocytes | | | | | | | | |
|---|---|---|---|---|---|---|---|---|---|
| Dose | Experiment 1[1] | | | Experiment 2[1] | | | Experiment 3[2] | | |
| (μg/ml) | PHA | ConA | 0 | PHA | ConA | 0 | PHA | ConA | 0 |
| | $^3$H—thymidine incorporation (CPM) | | | | | | | | |
| 0 | 102,566 | 41,592 | 330 | 133,182 | 57,604 | 693 | 44,028 | 17,866 | 1,081 |
| 1 | 109,750 | 46,576 | 335 | 125,109 | 56,166 | 479 | 111,379 | 31,276 | 844 |
| 3 | 105,730 | 45,919 | 386 | 112,918 | 65,598 | 447 | 122,275 | 34,096 | 884 |
| 10 | 144,867 | 52,455 | 333 | 143,780 | 73,484 | 460 | 145,795 | 36,080 | 1,061 |
| 30[3] | 171,005 | 36,546 | 437 | 176,089 | 56,454 | 344 | 129,103 | 13,790 | 463 |

[1] With lymphocytes from fresh blood
[2] With thawed lymphocytes which had been stored in nitrogen
[3] Cytotoxic effects already present

TABLE 4

| | Effect of ciprofloxacin on the specific, allogeneic activation of human blood lymphocytes | | | | | | |
|---|---|---|---|---|---|---|---|
| | Dose (μg/ml) | | | | | | |
| Experiments | 0 | 0.1 | 0.3 | 1 | 3 | 10 | 30[2] |
| | $^3$H—thymidine incorporation (CPM) | | | | | | |
| No. 1 CO[1] | 4,890 | | | | | | |
| Test | 17,252 | 21,310 | 26,964 | 28,982 | 27,841 | 32,733 | 28,900 |
| No. 2 CO | 946 | | | | | | |
| Test | 42,292 | 64,461 | 82,315 | 87,12 | 82,933 | 72,662 | 34,988 |
| No. 3 CO | 245 | | | | | | |
| Test | 11,679 | 21,768 | 26,564 | 20,314 | 13,964 | 15,142 | 4,632 |

[1] Autologous control: lymphocytes treated with mitomycin C as the stimulator
[2] Already cytotoxic effects present

PREPARATION EXAMPLES

EXAMPLE 1

Ciprofloxacin

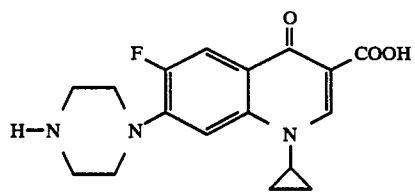

A mixture of 19.7 g of 7-chloro-1-cyclopropyl-6-fluoro-1,4-dihydro-4-oxoquinoline-3-carboxylic acid, 30.1 g of anhydrous piperazine and 100 ml of dimethyl sulphoxide is heated at 135°–140° C. for 2 h. The solvent is removed by distillation under high vacuum, and the residue is suspended in H₂O, filtered off with suction and washed with water. For further purification, the moist crude product is boiled with 100 ml of water, filtered with suction at room temperature, washed with H₂O and dried to constant weight in a vacuum drying oven over CaCl₂ at 100° C. 19.6 g of 1-cyclopropyl-6-fluoro-1,4-dihydro-4-oxo-7-(1-piperazinyl)-quinoline-3-carboxylic acid of decomposition point 255°–257° C. are obtained.

The compound prepared in Example 1 is dissolved in 50 ml of hot 10% hydrochloric acid. The solution is filtered, 150 ml of ethanol are added, then it is cooled in ice, and the product is filtered off with suction, washed with alcohol and dried in vacuo at 100° C.

18.5 g of 1-cyclopropyl-6-fluoro-1,4-dihydro-4-oxo-7-(1-piperazinyl)-quinoline-3-carboxylic acid hydrochloride are obtained as colorless crystals of decomposition point 308°–310° C.

EXAMPLE 2

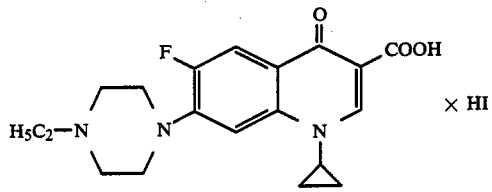

A mixture of 1.2 g of 1-cyclopropyl-6-fluoro-1,4-dihydro-4-oxo-7-(1-piperazinyl)-quinoline -3-carboxylic acid, 1.13 g of ethyl iodide, 0.73 g of triethylamine and 20 ml of N,N-dimethylformamide is heated at 70°–80° C. for 2.5 h. The solvent is removed by distillation in vacuo, and the residue is suspended in water. The product is filtered off with suction, washed with H₂O and pressed on a clay plate. 1.15 g of 1-cyclopropyl-6-fluoro-1,4-dihydro-4-oxo-7-(4-ethyl-1-piperazinyl)-quinoline-3-carboxylic acid hydroiodide of decomposition point 306° C. are obtained.

EXAMPLE 3

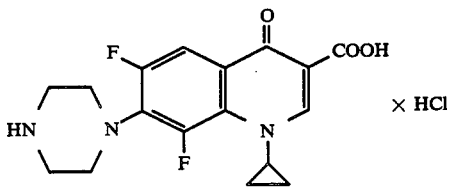

A mixture of 2.83 g (0.01 mol) of 1-cyclopropyl-6,7,8-trifluoro-1,4-dihydro-4-oxo-3-quinolinecarboxylic acid, 4.4 g (0.051 mol) of anhydrous piperazine and 30 ml of dry pyridine is refluxed for 6 hours. The solvent is removed in vacuo, the residue is taken up in 25 ml of water, the pH is adjusted to 1 with concentrated hydrochloric acid while cooling in ice, the precipitate is filtered off cold with suction, and washed with cold 10% strength hydrochloric acid and ethanol. After drying in vacuo at 100° C., 3.05 g of 1-cyclopropyl-6,8-difluoro-1,4-dihydro-4-oxo-7-(1-piperazinyl)-3-quinolinecarboxylic acid hydrochloride of decomposition point 354°–355° C. are obtained.

EXAMPLE 4

2.83 g (0.01 mol) of 1-cyclopropyl-6,7,8-trifluoro-1,4-dihydro-4-oxo-3-quinolinecarboxylic acid are reacted with 4 g (0.04 mol) of N-methylpiperazine in analogy to Example 3, and 3.6 g of 1-cyclopropyl-6,8-difluoro-1,4-dihydro-4-oxo-7-(4-methyl-1-piperazinyl)-3-quinolinecarboxylic acid hydrochloride of decomposition point 300°–303° C. are isolated.

It will be understood that the specification and examples are illustrative but not limitative of the present invention and that other embodiments within the spirit and scope of the invention will suggest themselves to those skilled in the art.

We claim:

1. An immunostimulating composition comprising an antigen and an immunostimulating effective amount of a cyclopropylquinolone-3-carboxylic acid of the formula

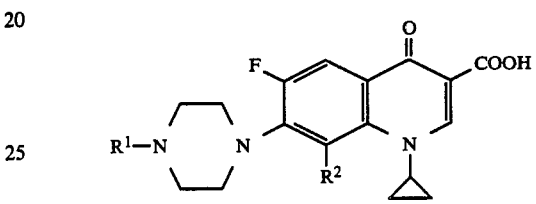

in which $R^1$ is hydrogen, methyl, ethyl or β-hydroxyethyl, and $R^2$ is hydrogen, chlorine or fluorine, or a physiologically tolerated salt thereof.

2. A composition according to claim 1, in which $R^1$ and $R^2$ are both hydrogen.

3. A composition according to claim 1, in which the immunostimulating cyclopropylquinolone-3-carboxylic acid is 1-cyclopropyl-6,8-difluoro-1,4-dihydro-4-oxo-7-(1-piperazinyl)-3-quinolinecarboxylic acid or a physiologically tolerated salt thereof.

4. A method of stimulating an immune response in a patient which comprises administering to such patient an immunostimulating effective amount of a 1-cyclopropylquinolone-3-carboxylic acid of the formula

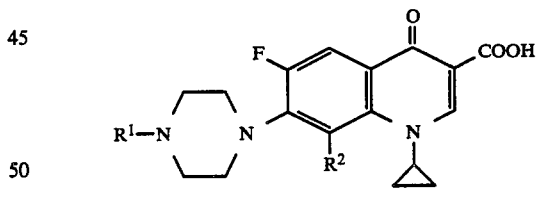

in which $R^1$ is hydrogen, methyl, ethyl or β-hydroxyethyl, and $R^2$ is hydrogen, chlorine or fluorine, or a physiologically tolerated salt thereof.

5. The method according to claim 4, in which the immunostimulating cyclopropylquinolone-3-carboxylic acid is 1-cyclopropyl-6,8-difluoro-1,4-dihydro-4-oxo-7-(1-piperazinyl)-3-quinolinecarboxylic acid or a physiologically tolerated salt thereof.

6. The method according to claim 3, wherein an additional stimulus is induced in the patient.

7. The method according to claim 4, wherein the additional stimulus is induced by administration of an antigen.

8. The method according to claim 3, in which $R^1$ and $R^2$ are both hydrogen.

* * * * *